United States Patent [19]

Davis et al.

[11] Patent Number: 5,922,741
[45] Date of Patent: *Jul. 13, 1999

[54] 5-AMINOPYRAZOLES USEFUL AS TYROSINE KINASE INHIBITORS

[75] Inventors: Peter David Davis, Oxford; Jeremy Martin Davis, Wokingham; David Festus Charles Moffat, Maidenhead, all of United Kingdom

[73] Assignee: Celltech Therapeutics Ltd., Berkshire, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/839,211

[22] Filed: Apr. 22, 1997

[30] Foreign Application Priority Data

Apr. 24, 1996 [GB] United Kingdom ............... 9608435

[51] Int. Cl.$^6$ ............... A61K 31/415; C07D 231/12; C07D 401/06
[52] U.S. Cl. ............... 514/341; 514/407; 546/279; 548/364.1; 548/365.7; 548/371.7
[58] Field of Search ............... 548/371.7, 364.1, 548/365.7; 546/279; 514/341, 407

[56] References Cited

U.S. PATENT DOCUMENTS

| | | | |
|---|---|---|---|
| 3,947,467 | 3/1976 | Verge et al. | 260/310 R |
| 4,012,495 | 3/1977 | Schmiechen et al. | 424/274 |
| 4,015,017 | 3/1977 | Gazave | 424/331 |
| 4,153,713 | 5/1979 | Huth et al. | 424/274 |
| 4,193,926 | 3/1980 | Schmiechen et al. | 260/326.5 |
| 4,303,649 | 12/1981 | Jones | 424/177 |
| 4,788,195 | 11/1988 | Torley et al. | 514/252 |
| 4,792,561 | 12/1988 | Walker et al. | 514/312 |
| 4,876,252 | 10/1989 | Torley et al. | 514/224.8 |
| 4,897,396 | 1/1990 | Hubele | 514/275 |
| 4,921,862 | 5/1990 | Walker et al. | 514/312 |
| 4,966,622 | 10/1990 | Rempfler et al. | 71/92 |
| 4,971,959 | 11/1990 | Hawkins | 514/150 |
| 5,124,455 | 6/1992 | Lombardo | 546/181 |
| 5,128,358 | 7/1992 | Saccomano et al. | 514/392 |

(List continued on next page.)

FOREIGN PATENT DOCUMENTS

| | | |
|---|---|---|
| 0 233 461 A2 | 8/1987 | European Pat. Off. . |
| 0 295 210 A1 | 12/1988 | European Pat. Off. . |
| 0 337 943 A2 | 10/1989 | European Pat. Off. . |
| 0 393 500 A1 | 10/1990 | European Pat. Off. . |
| 0 490 823 A1 | 6/1991 | European Pat. Off. . |
| 0 470 805 A1 | 2/1992 | European Pat. Off. . |
| 0 497 564 A1 | 8/1992 | European Pat. Off. . |
| 0 511 865 A1 | 11/1992 | European Pat. Off. . |
| 0 537 742 A2 | 4/1993 | European Pat. Off. . |
| 0 564 409 A1 | 10/1993 | European Pat. Off. . |
| 2 545 356 A1 | 11/1984 | France . |
| 250 1443 | 7/1975 | Germany . |
| 3-77872 | 4/1991 | Japan . |
| 3-77923 | 4/1991 | Japan . |
| 1285932 | 8/1972 | United Kingdom . |
| 1588639 | 4/1981 | United Kingdom . |

(List continued on next page.)

OTHER PUBLICATIONS

Chemical Abstracts, "Hypoglycemic Pharmaceuticals Containing Manzammide Derivatives", *Chem. Abstr.*, 1983, 99(6), No. 43558Z.

Dent et al., "Inhibition of eosinophil cyclic nucleotide PDE activity and opsonised zymosan–stimulated respiratory burst by 'type IV'–selective PDE inhibitors", *Br. J. Pharmacol.*, 1991, 103, 1339–1346.

Grammaticakis, "Contribution A L'Etude de L'Absortion Dans L'Ultraviolet Moyen Et Le Visible Des N–Aroyl–Arylamines. IV. 2,3–,3,4–et 2,4–, dimethoxybenzoylarylamines", *Bulletin DeLa Societa Chemique De France*, 1965, 848–858.

Heaslip et al., "Phosphodiesterase–IV Inhibition, Respiratory Muscle Relaxation and Bronchodilation by WAY–PDA–641", *J. Pharm. Exper. Ther.*, 1993, 268(2), 888–896.

Karlsson et al., "T–Lymphocyte and Inflammatory Cell Research in Asthma", Joller, G. et al. (eds.), Academic Press, 1993, 323–347.

(List continued on next page.)

*Primary Examiner*—Johann Richter
*Assistant Examiner*—Taofiq A. Solola
*Attorney, Agent, or Firm*—Woodcock Washburn Kurtz Mackiewicz & Norris LLP

[57] ABSTRACT

Compounds of general formula (1) are described:

$$\text{Ar} - \text{pyrazole} - CX^1NHR^1, NHR^2, R^3 \quad (1)$$

wherein

Ar is an optionally substituted aromatic or heteroaromatic group;

$X^1$ is an oxygen or sulphur atom;

$R^1$ is a hydrogen atom or a methyl group;

$R^2$ is a hydrogen atom or a group —$Alk^1$ or —$X^2Alk^1$ where $Alk^1$ is an optionally substituted aliphatic or heteroaliphatic group and $X^2$ is a —C(O)—, —C(S)—, or —S(O)$_n$ group where n is an integer 1 or 2;

$R^3$ is a hydrogen atom or a group —$Alk^2$, [where $Alk^2$ is as defined for $Alk^1$], —$X^2Alk^2$, —$Ar^1$ [where $Ar^1$ is an optionally substituted aromatic or heteroaromatic group], —$Alk^2Ar^1$, or —$X^2Alk^2Ar^1$;

and the salts, solvates, hydrates and N-oxides thereof.

The compounds are selective inhibitors of the protein tyrosine kinase p56$^{lck}$ and are of use in the prophylaxis and treatment of immune diseases, hyperproliferative disorders and other diseases in which inappropriate p56$^{lck}$ activity is believed to have a role.

16 Claims, No Drawings

U.S. PATENT DOCUMENTS

| | | | |
|---|---|---|---|
| 5,159,078 | 10/1992 | Rempfler et al. | 544/330 |
| 5,175,167 | 12/1992 | Zipperer et al. | 514/277 |
| 5,177,085 | 1/1993 | Naef | 514/307 |
| 5,236,918 | 8/1993 | Amschler et al. | 514/247 |
| 5,274,002 | 12/1993 | Hawkins | 514/530 |
| 5,298,511 | 3/1994 | Waterson | 514/311 |
| 5,326,898 | 7/1994 | Chandraratna | 560/17 |
| 5,340,827 | 8/1994 | Beeley et al. | 514/352 |
| 5,491,147 | 2/1996 | Boyd et al. | 514/247 |
| 5,521,184 | 5/1996 | Zimmermann | 514/252 |
| 5,550,137 | 8/1996 | Beeley et al. | 514/354 |
| 5,580,888 | 12/1996 | Warrellow et al. | 514/332 |
| 5,593,997 | 1/1997 | Dow et al. | 514/258 |
| 5,608,070 | 3/1997 | Alexander et al. | 546/270 |
| 5,622,977 | 4/1997 | Warrellow | 514/336 |
| 5,693,659 | 12/1997 | Head et al. | 514/357 |
| 5,723,460 | 3/1998 | Warrellow et al. | 514/247 |
| 5,739,144 | 4/1998 | Warrellow et al. | 514/277 |

FOREIGN PATENT DOCUMENTS

| | | |
|---|---|---|
| WO 87/06576 | 11/1987 | WIPO . |
| WO 91/15451 | 10/1991 | WIPO . |
| WO 91/16892 | 11/1991 | WIPO . |
| WO 92/00968 | 1/1992 | WIPO . |
| WO 92/06085 | 4/1992 | WIPO . |
| WO 92/06963 | 4/1992 | WIPO . |
| WO 92/07567 | 5/1992 | WIPO . |
| WO 92/12961 | 8/1992 | WIPO . |
| WO 92/19594 | 11/1992 | WIPO . |
| WO 92/19602 | 11/1992 | WIPO . |
| WO 93/10118 | 5/1993 | WIPO . |
| WO 93/19748 | 10/1993 | WIPO . |
| WO 94/02465 | 2/1994 | WIPO . |
| WO 94/10118 | 5/1994 | WIPO . |
| WO 94/12461 | 6/1994 | WIPO . |
| WO 94/13661 | 6/1994 | WIPO . |
| WO 94/14742 | 7/1994 | WIPO . |
| WO 94/20446 | 9/1994 | WIPO . |
| WO 94/20455 | 9/1994 | WIPO . |
| WO 95/09847 | 4/1995 | WIPO . |
| WO 95/09851 | 4/1995 | WIPO . |
| WO 95/09852 | 4/1995 | WIPO . |
| WO 95/09853 | 4/1995 | WIPO . |
| WO 95/17386 | 6/1995 | WIPO . |
| WO 95/31451 | 11/1995 | WIPO . |
| WO 95/35281 | 12/1995 | WIPO . |
| WO 95/35283 | 12/1995 | WIPO . |
| WO 95/53727 | 12/1995 | WIPO . |
| WO 96/14843 | 5/1996 | WIPO . |
| WO 97/09297 | 3/1997 | WIPO . |

OTHER PUBLICATIONS

Mathison et al., "Synthesis and Hypotensive Properties of Tetrahydroixoquinolines", *J. Med. Chem.*, 1973, 16(4), 332–336.

Miyaura, N. et al., "The Palladium–Catalyzed Cross–Coupling Reaction of Phenylboronic Acid with Haloarenes in the Presence of Bases", *Synth. Comm.*, 1981, 11, 513–519.

Takeuchi, I. et al., "On the Antimocrobial Activity and Syntheses of Carbanilide and Salicylanilide Derivatives", *Chem. Abstr.*, 1983, 98, No. 125577y.

Trost and Fleming (eds.), *Comprehensive Organic Synthesis*, Pergamon Press, New York, 1991, 3, 531–541.

Ashton, "Selective Type IV Phosphodiesterase Inhibitors as Antiasthmatic Agents. The Syntheses and Biological Activities of 3–(Cyclopentyloxy)–4–methyoxybenzamides and Analogues", *J. Med. Chem.*, 1994, 37, 1696–1703.

Beavo & Reifsnyder, "Primary Sequence of Cyclic Nucleotide Phosphodiesterase Isozymes and the Design of Selective Inhibitors" *TIPS*, 1990, 11, 150–155.

Buu–Hoi, N.P. et al., "Bromination of Some 1,2,2–Triarylethylenes" *J. of Organic Chemistry*, 1958, 1261–1263.

Buu–Hoi et al., "New Method for the Synthesis of ω,ω–Diarylacetophenones Aminated in the Aromatic Nucleus. Plynitration of Triarylethylenes", *Chem. Abstr.*, 1964, 61(13), 16006h.

Chan, A.C. et al., "The Role of Protein Tyrosine Kinases and Protein Tyrosine Phosphatases in T Cell Antigen Receptor Signal Transduction", *Annu. Rev. Immunol.*, 1994, 12, 555–592.

Daves, G.D. et al., "Pyrimidines. XIII. 2–and 6–Substituted 4–Pyrimidinecarboxylic Acids", *J. Of Hev. Chem.*, 1964, 1, 130–133.

Dietl, F. et al., "Chinone von Benzo–und Dibenzokroneneth-ern", *Synthesis*, 1985, 626–631.

El–Wakil et al., "Study of the proton magnetic resonance of methoxytamoxifen towards ortho–substitiution", *Chem. Abstr.*, 1992, 116, 255248t.

Geissler, J.F. et al., "Thiazolidine–Diones. Biochemical and Biological Activity of a Novel Class of Tyrosine Protein Kinase Inhibitors", *J. Of Biol. Chem.*, 1990, 265(36), 22255–22261.

Hanks, S.K. et al., "The eukaryotic protein kinase superfamily: kinase (catalytic) domain structure and classification", *FASEB J.*, 1995, 9, 576–596.

Hirose et al., "Styrene Derivatives and Electrophotographic Photoreceptor Containing Them", *Chem. Abstr.*, 1993, 118, 136183z.

Ishikura, M. et al., "An Efficient Synthesis of 3–Heteroarylpyridines via Diethyl–(3–pyridyl)–borane" *Synthesis*, 1984, 936–938.

Iwashita, S. et al., "Signal Transduction System for Growth Factor Receptors Associated with Tyrosine Kinase Activity: Epidermal Growth Factor Receptor Singalling and Its Regulation", *Cellular Signalling*, 1992, 4(2), 123–132.

Lisle, H. et al., "IL–2–Induced Eosinophilia in the Rat Pleural Cavity: The Effect of Dexamethasone and Indomethacin", *Br. J. Pharmacol.* 1993, 108, 230.

Livi et al., "Cloning and Expression of cDNA for a Human Low–$K_m$3 Rolipram–sensitive Cyclic AMP Phosphodiesterase", *Molecular and Cellular Biol.* 1990, 10(6), 2678–2686.

Manhas et al., "heterocyclic Compounds XII. Quinazoline Derivatives as Potential Antifertility Agents (1)" *J. Heterocyclic Chem.*, 1979, 16, 711–715.

Meyers, A.J. et al., "Oxazolines. XI. Synthesis of Functionalized Aromatic and Aliphatic Acids. A Useful Protecting Group for Carboxylic Acids Against Grignard and Hydride Reagents", *J. Org. Chem.* 1974, 39(18), 2787–2793.

Mezheritskaya, "Synthesis and properties of carboxonium het=erocyclic systems. VII. Synthesis and properties of 2–benzyl–substituted 1,3–dioxolanium salts", *Chem. Abstr.*, 1980, 93, 95160j, 635.

Mitsunobu, O., "The Use of Diethyl Azodicarboxylate and Triphenylphosphine in Synthesis and Transformation of Natural Products" *Synthesis*, 1981, 1–28.

Newton, A.C., "Protein Kinase C: Structure, Function, Regulation", *J. Biol. Chem.*, 1995, 270(48), 28495–28498.

Nicholson et al., "Differential Modulation of Tissue Function and Therapeutic Potential of Selective Inhibitors of Cyclic Nucleotide Phosphodiesterase Isoenzymes" *TIPS*, 1991, 12, 19–27.

O'Connor et al., "Voltammetry and Controlled Potential Oxidation of 3,4–dimethoxypropenylbenzene at a rotating platinum electrode in unbuffered acetonitrile and in acetonitrile–pyridine solution" *Chem. Abstr.*, 1964, 60(8) #10203.4.

Ohtani, Y. et al., "Studies on Pitch Problems Caused by Pulping and Bleaching of Tropical Woods. XIV. Chemistry of the Aurone Derivatives at the Conventional Bleaching Stages", *Acta Chem. Scand.*, 1982, 613–621.

Pines, J., "Cyclins and cyclin–dependent kinases: take your partners", *TIBS*, 1993, 18, 195–197.

Plé, N. et al., "Metalation of Diazines. XI. Directed Ortho–Lithiation of Fluoropyrimidines and Application to Synthesis of an Azacarboline", *J. Heterocylic Chem.*, 1994, 31, 1311–1315.

Porter et al., "Preparation of 6–phenyl–3–(5–tetrazolyl)-pyridin–=2 (H)–one Derivatives as Cyclic AMP–dependent Protein Kinase Agonists" *Chem. Abstr.*, 1992, 117(9), 90296n.

Ramalingam, Deshmukh and Sattur, "Synthesis and Pharmacology of 2,5–Disubstituted 1,3,4–Zxadiazoles" *J. Indian Chem. Soc.*, 1981, 58(3), 269–271.

Reddy et al., "Inhibition of Breast Cancer Cell Growth in Vitro by a Tyrosine Kinase Inhibitor" *Cancer Research*, 1992, 52, 3636–3641.

Sánchez, H.I. et al., "Formal Total Synthesis of β–Pipitzol", *Tetrahedron*, 1985, 41(12), 2355–2359.

Schneider et al., "Catechol Estrogens of the 1,1, 2–Triphenylbut–1–ene Type: Relationship Between Structure, Estradiol Receptor Affinity, Estrogenic and Antiestrogenic Properties, and Mammary Tumor Inhibiting Activities" *J. Med. Chem.*, 1986, 29, 1355–1362.

Seitz et al., "Fluorotamoxifen. A Caveat on the Generality of Electrophilic Destannylation" *Chem. Abstr.*, 1989, 111, 57133k.

Sharp, M.J. et al., "Synthetic Connections to the Aromatic Directed Metalation Reaction. Functionalized Aryl Boronic Acids by Ipso Borodesilylation; General Synthesis of Unsymmetrical iphenyls and n–Terphenyls", *Tetrahedron Lett.*, 1987, 28(43), 5093–5096.

Thompson, W.J. and Gaudino, J., "A General Synthesis of 5–Arylnicotinates" *J. Org. Chem.*, 1984, 49, 5237–5243.

Yeadon et al., "Mechanisms Contributing to Ozone–Induced Bronchial Hyperreactivity in Guinea Pigs", *Pulmonary Pharm.*, 1992, 5, 39–50.

Yoneda et al., "The Antiproliferative Effects of Tyrosine Kinase Inhibitors Tyrphostins on a Human Squamous Cell Carcinoma in Vitro and in Nude Mice" *Cancer Research*, 1991, 51, 4430–4435.

Sakakibara, K. et al., "Preparation of N–pyridyl–4–(benzyloxy) benzamides as Cardiotonics", *Chem. Abstr.*, 1988, 108, no. 131583p.

Tsutsumi, K. et al., "Preparation of (Dialkoxyphosphinoylmethyl) benzamides as Antihyperlipidemics", *Chem. Abstr.*, 1990, 113, no. 6599a.

Tominaga et al., "Polarized Ethylenes. IV [1]. Synthesis of Polarized Ethylenes Using Thioamides and Methyl Dithiocarboxylates and Their Application to Synthesis of Pyrazoles, Pyrimidines, Pyrazolo [3,4–d]pyrimidines, and 5–Aza [2.2.3]cyclazines", *J. Het. Chem.*, 1990, 27, 647–660.

Shioiri et al., "New Methods and Reagents in Organic Synthesis. 3. Diethyl Phosphorocyanidate: A New Reagent for C–Acylation", *J. Org. Chem.*, 1978, 43, 3631.

Collet et al., "Electrophilic Amination: Preparation and Use of N–Boc–3–(4–cyanophenyl) oxaziridine, a New Reagent That Transfers a N–Box Group to N–and C–Nucleophiles", *J. Org. Chem.*, 1993, 58, 4791–4793.

Chatterjee, A. et al., "Total Synthesis of Ring–C Aromatic 18–Nor Steroid", *Tetrahedron*, 1980, 36, 2513–2519.

Clayton, S.E. et al., "Direct Aromatic tert–Butylation during the Synthesis of Thiochroman–4–ones", *Tetrahedron*, 1993, 49(4), 939–946.

Collins, R.F. et al., "The Chemotherapy of Schistosomiasis. Part IV. Some Ethers of 4–Amino–2–methoxyphenol", *J. Chem. Soc.*, 1961, 1863–1879.

Geissler et al., "Biochemical and Biological Activity of a Novel Class of Tyrosine Protein Kinase Inhibitors", *J. Biol. Chem.*, 1990, 265(36), 22255–22261.

Griffin, R.W. et al., "1–Methyl–7–halo–2–naphthalenecarboxylic Acid Derivatives", *J. Organic Chem.*, 1964, 29(8), 2109–2116.

Gupta, A.S. et al., "Friedel–Crafts Condensation of Ethyl Allylmalonate with Anisole", *Tetrahedron*, 1967, 23, 2481–2490.

Hart et al., "Alkylation of Phenol with a Homoallylic Halide", *J. Am. Chem. Soc.*, 1963, 85, 3269–3273.

Johnson et al., "Identification of Retinoic Acid Receptor β Subtype Specific Agonists", *J. Med. Chem.*, 1996, 39(26), 5027–5030.

Lehmann, J. et al., "Lactones; XIII. Grignard Reaction Followed by Phase–Transfer Oxidation: A Convenient Synthesis of γ,γ–Distributed γ–Butyrolactones from γ–Butyrolactone", *Synthesis*, 1987, 1064–1067 (English abstract only).

Meyers, A.I. et al., "The Synthesis of 2–Pyridones from Cyclic Cyano Ketones. A New Aromatization Procedure for Dihydro–2–pyridones", *J. Org. Chem.*, 1964, 29, 1435–1438.

Kefalas, P. et al., "Signalling by the p60$^{c-src}$ Family of Protein–Tyrosine Kinases", *Int. J. Biochem. Cell Biol.*, 1995, 27(6), 551–563.

Pickett, W.C. et al., "Modulation of Eicosanoid Biosynthesis by Novel Pyridinylpyrimidines" *Ann. N.Y. Acad. Sci.*, 1994, 744, 299–305.

Spada, A.P. et al., "Small Molecule Inhibitors of Tyrosine Kinase Activity", *Exp. Opin. Ther. Patents*, 1995, 5(8), 805–817.

Yamaguchi, H., "Guanidinobenzene derivatives as anticoagulants", *Chem. Abstr.*, 1989, 110, 655 (Abstract Number 94706z).

Zimmermann, J. et al., "Phenylamino–Pyrimidine (PAP) Derivatives: A New Class of Potent and Selective Inhibitors of Protein Kinase C (PKC)", *Arch. Pharm.*, 1996, 329(7), 371–376.

Zimmermann, J. et al. "Phenylamino–Pyrimidine (PAP)— Derivatives: A New Class of Potent and Highly Selective PDGF–Receptor Autophosphorylation Inhibitors", *Bioorg. Med. Chem. Lett.*, 1996, 6(11), 1221–1226.

Zimmermann, J. et al., "Potent and Selective Inhibitors of the ABL–Kinase Phenylamino–Pyrimidine (PAP) Derivatives", *Bioorg. Med. Chem. Lett.*, 1997, 7(2), 187–192.

5-AMINOPYRAZOLES USEFUL AS TYROSINE KINASE INHIBITORS

This invention relates to a series of substituted pyrazoles, to processes for their preparation, to pharmaceutical compositions containing them, and to their use in medicine.

Protein kinases participate in the signalling events which control the activation, growth and differentiation of cells in response to extracellular mediators and to changes in the environment. In general, these kinases fall into two groups; those which preferentially phosphorylate serine and/or threonine residues and those which preferentially phosphorylate tyrosine residues [Hanks, S K, Hunter T, FASEB. J. 9, 576–596 (1995)]. The serine/threonine kinases include for example, protein kinase C isoforms [Newton A C, J. Biol. Chem. 270, 28495–28498 (1995)] and a group of cyclin-dependent kinases such as cdc2 [Pines J, Trends in Biochemical Sciences 18, 195–197 (1995)]. The tyrosine kinases include membrane-spanning growth factor receptors such as the epidermal growth factor receptor [Iwashita S and Kobayashi M. Cellular Signalling 4, 123–132 (1992)], and cytosolic non-receptor kinases such as $p56^{lck}$, $p59^{fyn}$, ZAP-70 and csk kinases [Chan C et al Ann. Rev. Immunol. 12, 555–592 (1994)].

Inappropriately high protein kinase activity has been implicated in many diseases resulting from abnormal cellular function. This might arise either directly or indirectly, for example by failure of the proper control mechanisms for the kinase, related for example to mutation, overexpression or inappropriate activation of the enzyme; or by over- or underproduction of cytokines or growth factors also participating in the transduction of signal upstream or downstream of the kinase. In all of these instances, selective inhibition of the action of the kinase might be expected to have a beneficial effect.

We have now found a series of 5-aminopyrazole derivatives which are potent and selective inhibitors of the protein tyrosine kinase $p56^{lck}$. The compounds are of use in the prophylaxis and treatment of immune diseases, hyperproliferative disorders and other diseases in which inappropriate $p56^{lck}$ activity is believed to have a role.

Thus according to one aspect of the invention, we provide a compound of formula (1):

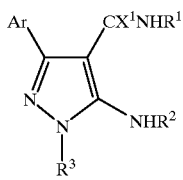

(1)

wherein
Ar is an optionally substituted aromatic or heteroaromatic group;
$X^1$ is an oxygen or sulphur atom;
$R^1$ is a hydrogen atom or a methyl group;
$R^2$ is a hydrogen atom or a group —$Alk^1$ or —$X^2Alk^1$ where $Alk^1$ is an optionally substituted aliphatic or heteroaliphatic group and $X^2$ is a —C(O)—, —C(S)—, or —$S(O)_n$ group where n is an integer 1 or 2;
$R^3$ is a hydrogen atom or a group —$Alk^2$, [where $Alk^2$ is as defined for $Alk^1$], —$X^2Alk^2$, —$Ar^1$ [where $Ar^1$ is an optionally substituted aromatic or heteroaromatic group], —$Alk^2Ar^1$, or —$X^2Alk^2Ar^1$;

and the salts, solvates, hydrates and N-oxides thereof.

Aromatic groups represented by the groups Ar or, when present, $Ar^1$ in compounds of formula (1) include for example mono- or bicyclic $C_{6-12}$ optionally substituted aromatic groups, for example optionally substituted phenyl, 1- or 2-naphthyl, 1- or 2-tetrahydronaphthyl, indanyl or indenyl groups.

Heteroaromatic groups represented by Ar or $Ar^1$ include for example $C_{1-9}$ optionally substituted heteroaromatic groups containing for example one, two, three or four heteroatoms selected from oxygen, sulphur or nitrogen atoms. In general, the heteroaromatic groups may be for example monocyclic or bicyclic heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example nine- to thirteen-membered heteroaromatic groups containing one, two or more heteroatoms selected from oxygen, sulphur or nitrogen atoms.

Particular examples of heteroaromatic groups represented by Ar or $Ar^1$ include optionally substituted pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, benzotriazolyl, isobenzothienyl, indolyl, isoindolyl, benzimidazolyl, imidazo[1,2-a]pyridyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl, 5,6,7,8-tetrahydroisoquinolinyl, or imidyl, e.g. succinimidyl, phthalimidyl, or naphthalimidyl such as 1,8-naphthalimidyl.

Optional substituents which may be present on the aromatic or heteroaromatic groups represented by Ar or $Ar^1$ include one, two, three or more groups, each represented by the group $R^4$. The substituent $R^4$ may be selected from an atom or group $R^5$ or —$Alk^3(R^5)_m$, where $R^5$ is a halogen atom, or an amino (—$NH_2$), substituted amino, nitro, cyano, hydroxyl (—OH), substituted hydroxyl, formyl, carboxyl (—$CO_2H$), esterified carboxyl, thiol (—SH), substituted thiol, —$COR^6$ [where $R^6$ is an —$Alk^3(R^5)_m$, aryl or heteroaryl group], —$CSR^6$, —$SO_3H$, —$SO_2R^6$, —$SO_2NH_2$, —$SO_2NHR^6$, $SO_2N[R^6]_2$, —$CONH_2$, —$CSNH_2$, —$CONHR^6$, —$CSNHR^6$, —$CON[R^6]_2$, —$CSN[R^6]_2$, —$NHSO_2H$, —$NHSO_2R^6$, —$N[SO_2R^6]_2$, —$NHSO_2NH_2$, —$NHSO_2NHR^6$, —$NCSO_2N[R^6]_2$, —$NHCOR^6$, —$NHCSR^6$, —$NHC(O)OR^6$, aryl or heteroaryl group; $Alk^3$ is a straight or branched $C_{1-6}$alkylene, $C_{2-6}$alkenylene or $C_{2-6}$alkynylene chain, optionally interrupted by one, two or three —O— or —S— atoms or —$S(O)_n$ or —$N(R^7)$— groups [where $R^7$ is a hydrogen atom or $C_{1-6}$alkyl, e.g. methyl or ethyl group]; and m is zero or an integer 1, 2 or 3.

When in the group —$Alk^3(R^5)_m$ m is an integer 1, 2 or 3, it is to be understood that the substituent or substituents $R^5$ may be present on any suitable carbon atom in —$Alk^3$. Where more than one $R^5$ substituent is present these may be the same or different and may be present on the same or different atom in —$Alk^3$. Clearly, when m is zero and no substituent $R^5$ is present the alkylene, alkenylene or alkynylene chain represented by $Alk^3$ becomes an alkyl, alkenyl or alkynyl group.

When $R^5$ is a substituted amino group it may be for example a group —$NHR^6$ [where $R^6$ is as defined above] or a group —$N[R^6]_2$ wherein each $R^6$ group is the same or different.

When $R^5$ is a halogen atom it may be for example a fluorine, chlorine, bromine, or iodine atom.

When $R^5$ is a substituted hydroxyl or substituted thiol group it may be for example a group —$OR^6$ or a —$SR^6$ or —$SC(NH_2+)NH_2$ group respectively.

Esterified carboxyl groups represented by the group $R^5$ include groups of formula —$CO_2Alk^4$ wherein $Alk^4$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyl-oxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^4$ group include $R^5$ substituents described above.

When $Alk^3$ is present in or as a substituent $R^4$ it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupred by one, two, or three —O— or —S—, atoms or —S(O)—, —S(O)$_2$— or —N($R^7$)— groups.

Aryl or heteroaryl groups represented by the groups $R^5$ or $R^6$ include mono- or bicyclic optionally substituted $C_{6-12}$ aromatic or $C_{1-9}$ heteroaromatic groups as described above for the groups Ar and $Ar^1$. The aromatic and heteroaromatic groups may be attached to the remainder of the compound of formula (1) by any carbon or hetero e.g. nitrogen atom as appropriate.

Particularly useful atoms or groups represented by $R^4$ include fluorine, chlorine, bromine or iodine atoms, or $C_{1-6}$alkyl, e.g. methyl or ethyl, $C_{1-6}$alkylamino, e.g. methylamino or ethylamino, $C_{1-6}$hydroxyalkyl, e.g. hydroxymethyl or hydroxyethyl, $C_{1-6}$alkylthiol e.g. methylthiol or ethylthiol, $C_{1-6}$alkoxy, e.g. methoxy or ethoxy, $C_{5-7}$cycloalkoxy, e.g. cyclopentyloxy, halo$C_{1-6}$alkyl, e.g. trifluoromethyl, halo$C_{1-6}$alkoxy, e.g. trifluoromethoxy, $C_{1-6}$alkylamino, e.g. methylamino or ethylamino, amino (—$NH_2$), amino$C_{1-6}$ alkyl, e.g. aminomethyl or aminoethyl, $C_{1-6}$dialkylamino, e.g. dimethylamino or diethylamino, imido, such as phthalimido or naphthalimido, e.g. 1,8-naphthalimido, 1,1,3-trioxobenzo-[d]thiazolidino, nitro, cyano, hydroxyl (—OH), formyl [HC(O)—], carboxyl (—$CO_2H$), —$CO_2Alk^4$ [where $Alk^4$ is as defined above], $C_{1-6}$ alkanoyl e.g. acetyl, thiol (—SH), thio$C_{1-6}$alkyl, e.g. thiomethyl or thioethyl, —$SC(NH_2+)NH_2$, sulphonyl (—$SO_3H$), $C_{1-6}$alkylsulphonyl, e.g. methylsulphonyl, aminosulphonyl (—$SO_2NH_2$), $C_{1-6}$ alkylaminosulphonyl, e.g. methylaminosulphonyl or ethylaminosulphonyl, $C_{1-6}$ dialkylaminosulphonyl, e.g. dimethylaminosulphonyl or diethylaminosulphonyl, phenylamino-sulphonyl, carboxamido (—$CONH_2$), optionally substituted $C_{1-6}$alkylaminocarbonyl, e.g. methylaminocarbonyl, ethylaminocarbonyl, propylaminocarbonyl, 2-aminoethylaminocarbonyl, aminopropylaminocarbonyl, N-(methoxycarbonyl)-2-amino-carbonyl, N-(methoxycarbonyl)-3-aminopropylaminocarbonyl, N-(butoxycarbonyl)-3-aminopropylaminocarbonyl, $C_{1-6}$ dialkylaminocarbonyl, e.g. dimethylaminocarbonyl or diethylaminocarbonyl, sulphonylamino (—$NCSO_2H$), $C_{1-6}$alkylsulphonylamino, e.g. methylsulphonylamino or ethyl-sulphonylamino, $C_{1-6}$ dialkylsulphonylamino, e.g. dimethylsulphonylamino or diethylsulphonylamino, optionally substituted phenylsulphonylamino, e.g. 2-, 3- or 4-substituted phenylsulphonylamino such as 2-nitrophenylsulphonylamino, aminosulphonylamino (—$NCSO_2NH_2$), $C_{1-6}$alkylamino-sulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, phenylaminosulphonyl-amino, $C_{1-6}$alkanoylamino, e.g. acetylamino, $C_{1-6}$alkanoylamino$C_{1-6}$alkyl, e.g. acetylaminomethyl, or $C_{1-6}$alkoxycarbonylamino, e.g. methoxycarbonylamino, ethoxycarbonylamino or t-butoxycarbonylamino groups.

Where desired, two $R^4$ substituents may be linked together to form a cyclic group such as a cyclic ether, e.g. a $C_{2-6}$alkylenedioxy group such as ethylenedioxy.

It will be appreciated that where two or more $R^4$ substituents are present, these need not necessarily be the same atoms and/or groups.

When the group —$Alk^1$ or —$Alk^2$ is present in the compounds of formula (1) it may be for example an optionally substituted $C_{1-10}$aliphatic or $C_{1-10}$ heteroaliphatic group.

Particular examples of aliphatic groups represented by —$Alk^1$ or —$Alk^2$ include optionally substituted straight or branched $C_{1-6}$alkyl, $C_{2-6}$alkenyl or $C_{2-6}$alkynyl groups. Particular heteroaliphatic groups include the aliphatic groups just recited but each additionally containing one, two, three or four heteroatoms selected from oxygen, sulphur or nitrogen atoms.

Thus, for example, —$Alk^1$ or —$Alk^2$ when present in compounds of formula (1) may be an optionally substituted —$CH_3$, —$CH_2CH_3$, —$(CH_2)_2CH_3$, —$CH(CH_3)_2$, —$(CH_2)_3CH_3$, —$CH(CH_3)CH_2CH_3$, —$CH_2CH(CH_3)_2$, —$C(CH_3)_3$, —$(CH_2)_4CH_3$, —$(CH_2)_5CH_3$, —$CHCH_2$, —$CHCHCH_3$, —$CH_2CHCH_2$, —$CHCHCH_2CH_3$, —$CH_2CHCHCH_3$, —$(CH_2)_2CHCH_2$, —$CHCH(CH_2)_2CH_3$, —$CH_2CHCHCH_2CH_2$, —$(CH_2)_2CHCHCH_3$, —$(CH_2)_3CHCH_2$ $CHCH_2$, —$CHCH(CH_2)_3CH_3$, —$CH_2CHCH(CH_2)_2CH_3$, —$(CH_2)_2CHCHCH_2CH_3$, —$(CH_2)_3CHCHCH_3$, or —$(CH_2)_4CH_2CH_2$ group, each of said groups, where appropriate, being optionally interrupted by one or two —O— or —S— atoms and/or —C(O)—, —C(S)—, —S(O)—, —S(O)$_2$—, —N($R^7$)—, —CON($R^7$)—, —OC(O)N($R^7$)—, —CSN($R^7$)—, —N($R^7$)CO, —N($R^7$)C(O)O—, —N($R^7$)CS—, —SON($R^7$)—, —SO$_2$N($R^7$)—, —N($R^7$)SO$_2$—, —N($R^7$)CON($R^7$)—, —N($R^7$)CSN($R^7$)—, —N($R^7$)SON($R^7$)— or —N($R^7$)SO$_2$N($R^7$)— groups.

Optional substituents which may be present on —$Alk^1$ or —$Alk^2$ in compounds of formula (1) include one, two, three or more $R^8$ substituents, where $R^8$ is as defined above for the substituent $R^4$.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g.

methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

It will be appreciated that depending on the nature of the substituents $R^1$, $R^2$, $R^3$, $R^4$ and $R^5$ the compounds of formula (1) may exist as geometrical isomers and/or may have one or more chiral centres so that enantiomers or diasteromers may exist. It is to be understood that the invention extends to all such isomers of the compounds of formula (1), and to mixtures thereof, including racemates.

In general in compounds of formula (1) the group $R^1$ is preferably a hydrogen atom.

$X^1$ in compounds of formula (1) is preferably an oxygen atom.

In another general preference, the group $R^2$ in compounds of formula (1) is preferably a hydrogen atom.

One particularly useful group of compounds according to the invention is that wherein Ar is an optionally substituted aromatic group, especially an optionally substituted phenyl or naphthyl group. In compounds of this type Ar may be in particular a phenyl group or a phenyl group substituted by one, two, three or more $R^4$ groups as defined herein. Especially useful Ar groups include phenyl or monosubstituted phenyl groups where the substituent is a $R^4$ group as defined herein. Particularly useful $R^4$ substituents in groups of this type include halogen atoms and optionally substituted $C_{1-6}$alkyl groups, especially a chlorine atom or a methyl group.

In a further preference, the group $R^3$ in compounds of formula (1) is an —$Alk^2$, —$X^2Alk^2$, —$Ar^1$, —$Alk^2Ar^1$ or —$X^2Alk^2Ar^1$ group. Particularly useful compounds of this type are those wherein $R^3$ is an —$Alk^2$ or $Ar^1$ group. Especially useful $R^3$ groups include optionally substituted $C_{1-6}$alkyl, optionally substituted phenyl or optionally substituted pyridyl groups. Particular groups of this type include t-butyl, phenyl or 2-pyridyl groups, each of said phenyl or pyridyl groups being optionally substituted by a group $R^4$. Particularly useful $R^4$ groups include halogen atoms or amino (—$NH_2$), nitro, methyl, ethyl, methoxy or ethoxy groups.

Compounds according to the invention are potent and selective inhibitors of the protein tyrosine kinase $p56^{lck}$. In particular, compounds of the invention inhibit the $p56^{lck}$ enzyme at concentrations at which they have little or no useful inhibitory action on other protein kinases, in particular ZAP-70, protein kinase C and Csk kinases. The ability of the compounds to act in this way may be simply determined by the tests described in the Examples hereinafter.

The compounds according to the invention are thus of particular use in the prophylaxis and treatment of diseases or disorders in mammals, especially humans, in which inappropriate protein tyrosine kinase action plays a role, and the invention extends to such a use. Particular examples of diseases and disorders in which inappropriate tyrosine kinase action plays a role include autoimmune diseases such as rheumatoid arthritis, multiple sclerosis and systemic lupus erythematosus, in transplant rejection, in graft v host disease, in hyperproliferative disorders such as tumours and psoriasis, and in diseases in which cells receive pro-inflammatory signals such as asthma, inflammatory bowel disease and pancreatitis.

For use as just described the compounds according to the invention may be administered as pharmaceutical compositions containing an amount of the compound effective in the prophylaxis or treatment of the disease or disorder. Thus according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The therapeutically effective amount of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols Ar, $X^1$, $R^1$, $R^2$, and $R^3$, when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1981]. In some instances, deprotection may be the final step in the synthesis of a compound of formula (1) and the processes according to the invention described hereinafter are to be understood to extend to such removal of protecting groups.

Thus according to a further aspect of the invention, a compound of formula (1) wherein $R^1$ and $R^2$ is each a hydrogen atom may be prepared by reaction of an alkene of formula (2):

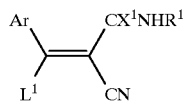

(2)

[wherein $L^1$ is an electron-donating leaving group], with a hydrazine $R^3NHNH_2$ or a salt thereof.

Particular examples of groups represented by $L^1$ include —OR, —OSO$_2$R, —SR and —N(R)$_2$ groups [where R is an aliphatic or heteroaliphatic group, as described herein for the group $Alk^1$ and may be for example an optionally substituted $C_{1-6}$alkyl group, such as a methyl or trifluoromethyl group].

The reaction may be performed in the presence of an organic solvent, for example an alcohol such as methanol or ethanol, or an ether, e.g. a cyclic ether such as tetrahydrofuran at an elevated temperature e.g. the reflux temperature, optionally in the presence of a base, e.g. an inorganic base such as an alkali metal base, e.g. sodium hydroxide or sodium carbonate.

Alkenes of formula (2) and hydrazines of formula $R^3NHNH_2$ are either known, [see for example Tominaga, Y, et al, J. Het. Chem., 27, 647–660, (1990)] and in some instances commercially available compounds, or may be obtained from known starting materials by methods analogous to those used for the preparation of the known compounds.

In another process according to the invention, a compound of formula (1) wherein $X^1$ is an oxygen atom and $R^1$ is a hydrogen atom may be prepared by heating a nitrile of formula (3):

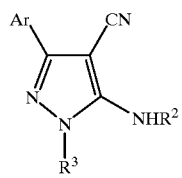

(3)

optionally either in the presence of a base, for example an inorganic base such as an alkali metal base, e.g. sodium hydroxide, in a solvent, for example an alcohol such as ethanol, or in the presence of a catalyst, for example a complex metal catalyst such as a palladium or ruthenium catalyst, e.g. tetrakis(triphenylphosphine)ruthenium dihydride in an inert organic solvent such as an ether, e.g. dimethoxyethane or dioxane or an aromatic hydrocarbon such as toluene or benzene.

The reaction may be performed at any suitable elevated temperature up to and above the reflux temperature depending on the nature of the reactants and solvents used.

Nitriles of formula (3) wherein $R^2$ is a hydrogen atom may be prepared by reaction of a dinitrile of formula (4):

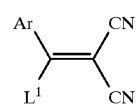

(4)

[where $L^1$ is as described above] with a hydrazine $R^3NHNH_2$ or a salt thereof using the reagents and conditions described above for the preparation of compounds of formula (1) from alkenes of formula (2).

Intermediate dinitriles of formula (4) are either known compounds [see for example Tominaga, Y et al ibid; and Shioiri, T & Hamada, Y, J. Org. Chem. 43, 3631 (1978)] or may be prepared from known starting materials by methods analogous to those used for the preparation of the known compounds, for example as described in the Examples hereinafter. Thus, for example, in one general process malononitrile may be reacted with an appropriate acid ArCO$_2$H or activated derivative thereof followed where necessary by generation of the leaving group $L^1$, for example by treating any ArCOCH(CN)$_2$ compound so obtained with trifluoromethanesulphonic anhydride in the presence of a base such as collidine to obtain the desired dinitrile ArC($L^1$)C (CN)$_2$ where $L^1$ is a leaving group —OSO$_2$CF$_3$.

Where it is desired to obtain an intermediate of formula (3) wherein $R^2$ is other than a hydrogen atom this may be obtained by interconversion of the corresponding compound of formula (3) wherein $R^2$ is a hydrogen atom, by alkylation or acylation, as described hereinafter for the interconversion of compounds of formula (1).

Compounds of formula (1) may also be prepared by interconversion of other compounds of formula (1) and it is to be understood that the invention extends to such interconversion processes. Thus, for example, standard substitution approaches employing for example alkylation, arylation, acylation, thioacylation, sulphonylation, formylation or coupling reactions may be used to add new substitutents to and/or extend existing substituents in compounds of formula (1). Alternatively existing substituents in compounds of formula (1) may be modified by for example oxidation, reduction or cleavage reactions to yield other compounds of formula (1).

The following describes in general terms a number of approaches which can be employed to modify existing Ar, $R^1$, $R^2$, and $R^3$ groups in compounds of formula (1). It will be appreciated that each of these reactions will only be possible where one or more appropriate functional groups exist in the compound of formula (1).

Thus, for example alkylation or arylation of a compound of formula (1), for example to introduce a group $Alk^1$ or $Ar^1$ may be achieved by reaction of the compound with a reagent $Alk^1L^2$ or $Ar^1L^2$, where $L^2$ is a leaving group. This reaction is particularly suitable for alkylation or arylation of compounds of formula (1) where $R^2$ is a hydrogen atom.

Leaving groups represented by $L^2$ include halogen atoms such as iodine, chlorine or bromine atoms or sulphonyloxy groups such as alkyl- or arylsulphonyloxy groups, e.g. methylsulphonyloxy or p-toluenesulphonyloxy.

The alkylation or arylation reaction may be carried out in the presence of a base, e.g. an inorganic base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran, at around 0° C. to around 40° C.

Alkylation as just described may also be used at low temperature in the preparation of a compound of formula (1) wherein $R^1$ is a methyl group from the corresponding compound of formula (1) in which $R^1$ is a hydrogen atom.

In another general example of an interconversion process, a compound of formula (1) may be acylated or thioacylated, for example to introduce a group —C(O)$Alk^1$ or —C(S)$Alk^1$. The reaction may be performed for example with an acyl or thioacyl halide or anhydride in the presence of a base, such as a tertiary amine e.g. triethylamine in a solvent such as a halogenated hydrocarbon, e.g. dichloromethane at for example ambient temperature, or by reaction with a thioester in an inert solvent such as tetrahydrofuran at a low temperature such as around 0° C. The reaction is particularly suitable for use with compounds of formula (1) where $R^2$ is a hydrogen atom.

Compounds of formula (1) may be prepared in another general interconversion reaction by sulphonylation, for example by reaction of the compound with a reagent $R^6S(O)_nL^2$ where $L^2$ is a leaving group as described above in the presence of a base, for example an inorganic base such as sodium hydride in a solvent such as an amide, e.g. a substituted amide such as dimethylformamide at for example ambient temperature. The reaction may in particular be performed with compounds of formula (1) in which Ar and/or $Ar^1$ possesses a primary or secondary amino group.

In further examples of interconversion reactions according to the invention compounds of formula (1) may be prepared from other compounds of formula (1) by modification of existing functional groups in the latter.

Thus in one example, ester groups —$CO_2Alk^4$ in compounds of formula (1) may be converted to the corresponding acid [—$CO_2H$] by acid- or base-catalysed hydrolysis depending on the nature of the group $Alk^4$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol.

In a second example, —$OR^6$ [where Alk represents an alkyl group such as methyl group] groups in compounds of formula (1) may be cleaved to the corresponding alcohol —OH by reaction with boron tribromide in a solvent such as a halogenated hydrocarbon, e.g. dichloromethane at a low temperature, e.g. around –78° C.

In another example, alcohol —OH groups in compounds of formula (1) may be converted to a corresponding —$OR^6$ group by coupling with a reagent $R^6OH$ in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NH_2$] groups in compounds of formula (1) may be obtained, in another example, by reaction of a corresponding amine [—$NH_2$] with sulphamide in the presence of an organic base such as pyridine at an elevated temperature, e.g. the reflux temperature.

In a further example, amine [—$NH_2$] groups in compounds of formula (1) may be obtained by hydrolysis from a corresponding imide by reaction with hydrazine in a solvent such as an alcohol, e.g. ethanol at ambient temperature.

In another example, a nitro [—$NO_2$] group may be reduced to an amine [—$NH_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

In a further example, amide [—$CONHR^6$] groups in compounds of formula (1) may be obtained by coupling a corresponding acid [—$CO_2H$] or an active derivative thereof, e.g. an acid anhydride, imide or halide, with an amine $R^6NH_2$. The coupling reaction may be performed using standard conditions for reactions of this type. Thus for example the reaction may be carried out in a solvent, for example an inert organic solvent such as an amide, e.g. a substituted amide such as dimethylformamide, at a low temperature, e.g. –30° C. to ambient temperature, optionally in the presence of a base, e.g. an organic base such as a cyclic amine, e.g. N-methylmorpholine, and where necessary in the presence of a condensing agent, for example a diimide such as 1-(3-dimethylaminopropyl)-3-ethylcarbodiimide.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

The following Examples illustrate the invention.

All temperatures are in °C. The following abbreviations are used: THF—tetrahydrofuran; DMF—dimethylformamide; DMSO—dimethylsulphoxide

EXAMPLE 1

5-Amino-1-tert-butyl-3-(4'-chlorophenyl)pyrazole-4-carboxamide

To a solution of tert-butyl hydrazine hydrochloride (523 mg, 3.50 mmol) in ethyl alcohol (20 ml) was added powdered sodium hydroxide (168 mg, 4.20 mmol), followed by 3-(4-chlorophenyl)-2-cyano-3-methylthioacrylamide (884 mg, 3.50 mmol) and the mixture was heated at reflux for 4 h. On cooling, the solvent was removed under reduced pressure and the residue partitioned between water (80 ml) and ethyl acetate (80 ml). The aqueous layer was further extracted with ethyl acetate (2×80 ml) and the combined organic layers were washed with brine (1×100 ml), dried (MgSO$_4$) and concentrated under reduced pressure. The residue was subjected to column chromatography (SiO$_2$, 45–75% ethyl acetate-hexane) to afford the title compound (780 mg) after recrystallisation from methanol as a colorless solid m.p. 156°. $\delta_H$ (d$^6$ DMSO) 1.66 (9H, s), 5.16 (2H, br s), 5.68 (2H, br s), 7.42 (2H, dt, J 8.6, 2.1 Hz), and 7.51 (2H, dt, J 8.7, 2.1 Hz).

The acrylamide starting material was prepared according to the method of Y Tominaga et al, J. Het. Chem (1990), 27, 647–660 [see for example page 653 describing the preparation of compound 8h].

The following compound was prepared in a similar manner:

EXAMPLE 2
5-Amino-3-(4'-chlorophenyl)-1H-pyrazole-4-carboxamide

From 3-(4-chlorophenyl)-2-cyano-3-methylthioacrylamide (290 mg, 1 mmol) and hydrazine monohydrate (60 mg, 1.2 mmol) to give the title compound (60 mg) after recrystallisation from ethyl acetate as a colourless solid, m.p. 224°. $\delta_H$ (d$^6$ DMSO) Minor Tautomer 5.18 (2H br s), 6.25 (2H, brs), 7.52 (4H, m), 12.18 (1H, brs), Major Tautomer 5.95 (2H, brs), 6.25 (2H, br s), 7.52 (4H, m), and 11.92 (1 H, br s).

EXAMPLE 3
5-Amino-1-tert-butyl-3(4'-trifluoromethylphenyl)pyrazole-4-carboxamide To a solution of 5-amino-1-tert-butyl-4-cyano-3-(4'-trifluoromethylphenyl)pyrazole (308 mg, 1.0 mmol) in ethanol (15 ml) was added 10M sodium hydroxide (3 ml) and the mixture heated at reflux for 72 h. On cooling, ethanol was removed under reduced pressure and water (50 ml) added. The resulting precipitate was collected by filtration, and washed with water (2×25 ml), to give the title compound (200 mg) as a colorless solid after recrystallisation from ethyl acetate m.p. 210–211°. $\delta_H$ (CDCl$_3$) 1.67 (9H, s), 5.16 (2H, br s), 5.69 (2H, br s), and 7.71 (4H, s).

The pyrazole starting material for this reaction was prepared as follows:
5-Amino-1-tert-butyl-4-cyano-3-(4'-trifluoromethylphenyl)pyrazole To a solution of 2-(4-trifluoromethylbenzoyl)propanedinitrile (1.70 g, 7.15 mmol) in CH$_2$Cl$_2$ (60 ml), was added collidine (1.89 ml, 14.3 mmol) followed by trifluoromethanesulphonic anhydride (1.45 ml, 8.58 mmol) and the mixture stirred at room temperature for 2 h. The reaction was concentrated under reduced pressure and the residue dissolved in THF (100 ml). This was added to a suspension of tert-butyl hydrazine hydrochloride (0.98 g, 7.86 mmol) and sodium carbonate (1.14 g, 10.73 mmol) in THF and heated at reflux for 2.5h. The reaction was again concentrated under reduced pressure, the residue dissolved in ethyl acetate (100ml), washed with 2M hydrochloric acid (1×100 ml), water (1×100 ml) and brine (1×100 ml), dried (MgSO$_4$) and solvent then removed under reduced pressure. The resulting solid was subjected to column chromatography to give the title compound (700 mg) as a pale pink solid after recrystallisation from ether, m.p. 155–156°. $\delta_H$ (CDCl$_3$) 1.68 (9H, s), 4.46 (2H, br s), 7.66 (2H, d, J 8.0 Hz), and 8.03 (2H, d, J 8.0 Hz).

The dinitrile starting material for this reaction was prepared as follows:
2-(4-Trifluoromethylbenzoyl)propanedinitrile To a solution of α, α', α"-trifluoro-p-toluic acid (4.56 g, 24.0 mmol) and malononitrile (1.45 g, 21.8 mmol) in DMF (50 ml) at 0° was added diethylcyanophosphonate (3.65 ml, 24.0 mmol) followed by triethylamine (9.40 ml, 69.8 mmol) and the mixture was stirred at 25° for 16 h. The reaction was concentrated under reduced pressure. The residue was dissolved in ethyl acetate (150 ml) and washed with 2 M hydrochloric acid (2×100 ml) and then with saturated NaHCO$_3$ (3×150 ml). The basic layers were acidified to pH 1 with 6M hydrochloric acid and extracted with ethyl acetate (3×125 ml). The combined organic layers were dried (MgSO$_4$) and concentrated under reduced pressure to give the title compound (1.90 g) as an orange solid which was not purified. $\delta_H$ (CDCl$_3$) 7.73 (4H, s), and 10.70 (1H, br s).

The following title compounds and intermediates of Examples 4–8 were prepared in a similar manner to the title compound and intermediates of Example 3.

EXAMPLE 4
5-Amino-1-tert-butyl-3-(3-furyl)pyrazole-4-carboxamide

From 5-amino-1-tert-butyl-4-cyano-3-(3-furyl)pyrazole (500 mg, 2.17 mmol) to give the title compound (340 mg) as a colourless solid m.p. 177°. $\delta_H$ (CDCl$_3$) 1.65 (9H, s), 5.48 (2H, br s), 5.66 (2H, br s), 6.62 (1H, dd, J 1.8, 0.8 Hz), 7.51 (1H, t, J 1.6 Hz), and 7.68 (1 H, dd, J 1.6, 0.9 Hz).

The pyrazole starting material was obtained from 2-(3-furoyl)propanedinitrile as an orange solid m.p. 98–99°. $\delta_H$ (CDCl$_3$) 1.69 (9H, s), 6.83 (1H, dd, J 1.7, 0.8 Hz), 7.44 (1H, t, J 1.7 Hz) and 7.98 (1H, m). The 2-(3-furoyl)propanedinitrile was obtained from 3-furoic acid as an off-white solid. $\delta_H$ (d$^6$ DMSO) 6.77 (1H, dd, J 1.8, 0.8 Hz), 7.70 (1H, t, J 1.7 Hz), 8.14 (1H, dd, J 1.5, 0.8 Hz), and 8.89 (1H, br s).

EXAMPLE 5
5-Amino-1-tert-butyl-3-(3-thienyl)pyrazole-4-carboxamide

From 5-amino-1-tert-butyl-4-cyano-3-(3-thienyl)pyrazole (492 mg, 2.0 mmol) to give the title compound (60 mg), as a colourless solid. m.p. 173–174° $\delta_H$ (CDCl$_3$) 1.71 (9H, s), 4.51 (2H, br s), 5.78 (2H, br s), 7.29 (1H, dd, J 4.9, 1.2 Hz), 7.47 (1H, dd, J 4.9, 3.0 Hz) and 7.60 (1H, m).

The pyrazole starting material was obtained from 2-(3-thienoyl)propanedinitrile as an off-white solid m.p. 132–133°. $\delta_H$ (CDCl$_3$) 1.67 (9H, s), 4.35 (2H, br s), 7.34 (1H, dd, J 5.0, 3.0 Hz), 7.59 (1H, dd, J 5.0, 1.2 Hz), and 7.84 (1H, dd, J 3.0, 1.3 Hz). The 2-(3-thienoyl)propanedinitrile was obtained from 3-thiophenecarboxylic acid as a yellow solid m.p. 142–145° $\delta_H$ (d$^6$ DMSO) 6.86 (1H, br s), 7.38 (1H, dd, J 5.1, 1.3 Hz), 7.52 (1H, dd, J 5.1, 2.9 Hz) and 7.99 (1H, dd, J 3.0, 1.3 Hz).

EXAMPLE 6
5-Amino-1-tert-butyl-3-(4-tolyl)pyrazole-4-carboxamide

From 5-amino-1-tert-butyl-4-cyano-3-(4-tolyl)pyrazole (460 mg, 1.81 mmol) to give the title compound (128 mg) as a colorless solid, m.p. 240–242°. $\delta_H$ (d$^6$ DMSO) 1.55 (9H, s), 2.34 (3H, s), 6.26 (2H, s), 7.24 (2H, d, J 8.0 Hz), and 7.33 (2H, d, J 8.0 Hz).

The pyrazole starting material was obtained from 2-(4-toluoyl)propanedinitrile as a yellow solid m.p. 163°. $\delta_H$ (CDCl$_3$) 1.67 (9H, s), 2.36 (3H, s), 4.30 (2H, br s), 7.20 (2H, d, J 8.2 Hz) and 7.80 (2H, d, J 8.2 Hz). The 2-(4-toluoyl)propanedinitrile was obtained from p-toluic acid as an off-white solid m.p. >190° (decomp.). $\delta_H$ (d$^6$ DMSO) 2.35 (3H, s), 7.27 (2H, d, J 8.0 Hz), 7.52 (2H, d, J 8.0 Hz), and 10.82 (1H, br s).

EXAMPLE 7
5-Amino-1-tert-butyl-3-(3,4,5-trimethoxyphenyl)pyrazole-4-carboxamide From 5-amino-1-tert-butyl-4-cyano-3-(3,4,5-trimethoxyphenyl)pyrazole (443 mg, 1.34 mmol) to give the title compound (30 mg) as a colourless solid m.p. 180–192°. $\delta_H$ (d⁶ DMSO) 1.55 (9H, s), 3.69 (3H, s), 3.78 (6H, s), 6.29 (2H, br s), and 6.71 (2H, s).

The pyrazole starting material was obtained from 2-(3,4,5-trimethoxy-benzoyl)propanedinitrile as an off-white solid m.p. 158–160°. $\delta_H$ (CD₃OD) 1.64 (9H, s), 3.79 (3H, s), 3.87 (6H, s), 4.80 (2H, s) and 7.14 (2H, s). The 2-(3,4,5-trimethoxybenzoyl)propanedinitrile was obtained from 3,4,5-trimethoxybenzoic acid as an off-white solid m.p. >140° (decomp). $\delta_H$ (d⁶ DMSO) 3.69 (3H, s), 3.75 (6H, s), 3.95 (1H, br s), and 6.99 (2H, s).

EXAMPLE 8

From 5-amino-1-tert-butyl-4-cyano-3-(2-naphthyl)pyrazole (220 mg, 0.8 mmol) to give the title compound (44 mg) as a colourless solid m.p. 224–225° C. $\delta_H$(CDCl₃) 1.69 (9H, s), 5.22 (2H, br s), 5.71 (2H, br s), 7.50–7.54 (2H, m), 7.65 (1H, dd, J 8.4, 1.6 Hz), 7.80–7.93 (3H, m), and 8.04 (1H, s).

The pyrazole starting material was obtained from 2-(2-naphthoyl)-propanedinitrile as a colourless solid m.p. 121°. $\delta_H$ (CDCl₃) 1.71 (9H, s), 4.38 (2H, br s), 7.45–7.51 (2H, m), 7.81–7.93 (3H, m), 8.05 (1H, dd, J 8.6, 1.8 Hz), and 8.41 (1H, s). The 2-(2-naphthoyl)propanedinitrile was obtained from 2-naphthoic acid as a yellow solid m.p. 195° (decomp.). $\delta_H$ (CDCl₃) 7.57–7.66 (2H, m), 7.71 (1H, dd, J 8.3, 1.7 Hz), 7.89 (1H, d, J 7.6 Hz), 7.94 (2H, d, J 8.3 Hz), and 8.26 (1 H. s).

EXAMPLE 9
5-Amino-1-phenyl-3-(4-tolyl)pyrazole-4-carboxamide

From 5-amino-4-cyano-1-phenyl-3-(4-tolyl)pyrazole (185 mg, 0.68 mmol) in a similar manner to the compound of Example 3 to give the title compound (29 mg) as a colourless solid m.p. 186–187° $\delta_H$ (CDCl₃) 2.41 (3H, s), 5.33 (2H, br s), 5.74 (2H, br s), 7.28 (2H, d, J 8.1 Hz), 7.36–7.41 (1H, m), 7.48–7.53 (3H, m), 7.54 (1H, m), and 7.61 (2H, d, J 8.6 Hz).

The pyrazole starting material for the above process was prepared as a colourless solid m.p. 169–170° $\delta_H$ (CDCl₃) 2.39 (3H, s), 4.64 (2H, br s), 7.16–7.32 (3H, m), 7.41–7.59 (4H, m), and 7.87 (2H, d, J 8.2 Hz) from phenylhydrazine and 2-(4-toluoyl)propanedinitrile in a similar manner to the intermediate pyrazole of Example 3.

EXAMPLE 10
5-Amino-1-tert-butyl-3-(4-methoxycarbonylphenyl)pyrazole-4-carboxamide A mixture of 5-amino-1-tert-butyl-4-cyano-3-(4-methoxycarbonylphenyl)pyrazole (448 mg, 1.5 mmol) and tetrakis(triphenylphosphine)ruthenium dihydride in dimethoxyethane (1 ml) and water (54 μl) was heated at 120° under a nitrogen atmosphere in a sealed tube for 18 h. The reaction was concentrated under reduced pressure and the residue subjected to column chromatography (silica 4% methanol-CH₂Cl₂) to give the title compound (170 mg) after recrystallisation from ethyl acetate as a colourless solid m.p. 237–239°. $\delta_H$(CDCl₃) 1.67 (9H, s), 4.39 (3H, s), 5.10 (2H, br s), 5.69 (2H, br s), 7.66 (2H, d, J 8.2 Hz), and 8.11 (2H, d, J 8.3 Hz).

The pyrazole starting material used in the above process was prepared as a light yellow solid m.p. 202–203°. $\delta_H$ (CDCl₃) 1.69 (9H, s), 3.93 (3H, s), 4.39 (2H, br s), 8.00 (2H, dt, J 7.6, 1.4 Hz), and 8.08 (2H, dt, J 8.8, 2.0 Hz) from 2-(4-methoxycarbonylbenzoyl)propanedinitrile in a similar manner to the intermediate pyrazole of Example 3.

The 2-(4-methoxycarbonylbenzoyl)propanedinitrile was obtained from monomethylterephthalate as an orange solid m.p. 153–160° (decomp.). $\delta_H$ (d⁶ DMSO) 3.85 (3H, s), 6.62 (1H, br s), 7.65 (2H, dt, J 8.6,1.9 Hz), and 7.93 (2H, dt, J 8.6, 2.0 Hz).

EXAMPLE 11
5-Amino-1-tert-butyl-3-phenylpyrazole-4-carboxamide

From 5-amino-1-tert-butyl-4-cyano-3-phenylpyrazole (720 mg, 3.0 mmol) in a similar manner to the compound of Example 3 to give the title compound as white crystals (92 mg) m.p. 177–178°. δH (CDCl₃) 7.54 (2H, m), 7.45 (3H, m), 5.69 (2H, br s), 5.21 (2H, br s) and 1.67 (9H, s).

The pyrazole starting material for the above process was obtained as described for the intermediate pyrazole of Example 3 from 2-benzoyl-propanedinitrile as a white crystalline solid m.p. 124–125°. δH (CDCl₃) 7.93 (2H, m), 7.42 (3H, m) 4.37 (2H, br s) and 1.68 (9H, s). The 2-benzoylpropanedinitrile was prepared from benzoic acid following the procedure described in Example 3 as a light yellow solid. δH (CDCl₃) 7.81 (2H, d, J 7.1 Hz), 7.66 (1H, t, J 7.1 Hz), 7.54 (2H, apparent t, J 7.1 Hz) and 6.10 (1H, br s).

EXAMPLE 12
5-Amino-3-(4-tolyl)-1-(3-trifluoromethoxyphenyl)pyrazole-4-carboxamide Powdered sodium hydroxide (88 mg, 2.2 mmol) was added to a solution of 3-trifluoromethoxyphenyl hydrazine hydrochloride (503 mg, 2.2 mmol) and 2-cyano-3-methylthio-3-(4-tolyl)acrylamide (464 mg, 2.0 mmol) in ethanol (20 ml) and the mixture heated at reflux for 18 h. On cooling, the solvent was removed under reduced pressure and the residue partitioned between water (80 ml) and ethyl acetate (100 ml). The aqueous layer was further extracted with ethyl acetate (2×80 ml) and the combined organic layers washed with brine (100 ml), dried (MgSO₄) and concentrated under reduced pressure. The crude product was recrystallised from isopropyl ether-heptane to give the title compound as white needles (320 mg) m.p. 177–179°. δH (CDCl₃) 7.70 (1H, m), 7.51 (1H, d, J 8.0 Hz), 7.38 (1H, d, J 8.0 Hz), 7.40 (1H, m), 7.09 (1H, d, J 7.9 Hz), 5.74 (2H, br s), 5.35 (2H, br s) and 2.42 (9H, s).

The 2-cyano-3-methylthio-3-(4-tolyl)acrylamide starting material was prepared according to the method of Tominaga et al J. Het. Chem. (1990) 27, 647–660 to give the compound as white crystals m.p. 200–210°. δH (CDCl₃) 7.31 (2H, d, J 8.4 Hz), 7.10 (2H, dt, J 8.4, 1.8 Hz), 6.12 (1H, br s), 5.54 (1H, br s), 2.41 (3H, s) and 1.90 (3H, s).

EXAMPLE 13
5-Amino-1-(4-bromophenyl)-3-(4-tolyl)pyrazole-4-carboxamide

The title compound was prepared from 2-cyano-3-methylthio-3-(4-tolyl)acrylamide (928 mg, 4.0 mmol), 4-bromophenylhydrazine hydrochloride (894 mg, 4.0 mmol) and sodium hydroxide (176 mg, 4.4 mmol) following the procedure used for the compound of Example 12. The crude product was subjected to column chromatography (SiO₂, 10% methanol in CH₂Cl₂) and recrystallisation from ethyl acetate to give the title compound as white crystals (470 mg) m.p. 222–223°. $\delta_H$ (CDCl₃) 7.63 (2H, dt, J 8.8, 2.2 Hz), 7.52 (2H, dt, J 8.5, 2.6 Hz), 7.48 (2H, d, J 7.4 Hz), 7.28 (2H, d, J 8.3 Hz), 5.74 (2H, br s), 5.29 (2H, br s), 2.41 (3H, s).

EXAMPLE 14
5-Amino-1-[(ethoxycarbonyl)methyl]-3-(4-tolyl)pyrazole-4-carboxamide The title compound was prepared from 2-cyano-3-methylthio-3-(4-tolyl)acrylamide (425 mg, 1.83 mmol), ethyl hydrazinoacetate hydrochloride (311 mg, 2.01 mmol) and sodium hydroxide (80 mg, 2.01 mmol) following the procedure used for the compound of Example 12. The crude product was subjected to column chromatography (SiO$_2$, 10% methanol in CH$_2$Cl$_2$) and was recrystallised from ethyl acetate to give the title compound as white crystals (152 mg) m.p. 179°. δH (CDCl$_3$) 7.43 (2H, d, J 8.1 Hz), 7.26 (2H, d, J 8.1 Hz), 5.56 (2H, br s), 5.22 (2H, br s), 4.77 (2H, s), 4.27 (2H, q, J 7.2 Hz), 2.40 (3H, s) and 1.32 (3H, t, J 7.2 Hz).

EXAMPLE 15
5-Amino-1-(2-pyridyl)-3-(4-tolyl)pyrazole-4-carboxamide

The title compound was prepared from 2-cyano-3-methylthio-3-(4-tolyl)acrylamide (4.64 mg, 2.0 mmol) and 2-hydrazinopyridine (218 mg, 2.0 mmol) following the procedure used for the compound of Example 12. The title compound was obtained as a white crystalline solid (350 mg) m.p. 244–247°. δH (d$^6$DMSO) 8.46 (1H, dm, J 5.0 Hz), 7.97 (1H, ddd, J 8.4, 7.4, 1.9 Hz), 7.85 (1H, d, J 8.4 Hz), 7.68 (2H, br s), 7.47 (2H, d, J 8.1 Hz), 7.31 (2H, d, J 7.6 Hz), 7.29 (1H, signal obscured by overlapping d), 3.30 (2H, s) and 2.37 (3H, s). MS (ES$^+$) 294 (MH$^+$, 100%).

EXAMPLE 16
5-Amino-1-(1-naphthyl)-3-(4-tolyl)pyrazole-4-carboxamide

The title compound was prepared from 2-cyano-3-methylthio-3-(4-tolyl) acrylamide (464 mg, 2.0 mmol), 1-naphthyl hydrazine hydrochloride (389 mg, 2.0 mmol) and sodium hydroxide (88 mg, 2.2 mmol) following the procedure used for the compound of Example 12. The crude product was subjected to column chromatography (SiO$_2$, 50–60% ethyl acetate in hexane) and was recrystallised from diethylether to give the title compound as pink crystals (185 mg) m.p. 195°. δH (CDCl$_3$) 8.00 (1H, d, J 8.3 Hz), 7.95 (1 H., m), 7.73–7.55 (7H, m), 7.30 (2H, d, J 8.3 Hz), 5.52 (2H, br s), 5.16 (2H, br s) and 2.42 (3H, s).

EXAMPLE 17
5-Amino-1-(2-tolyl)-3-(4-tolyl)pyrazole-4-carboxamide

The title compound was prepared from 2-cyano-3-methylthio-3-(4-tolyl) acrylamide (464 mg, 2.0 mmol), 2-tolylhydrazine hydrochloride (350 mg, 2.2 mmol) and sodium hydroxide (88 mg, 2.2 mmol) following the procedure used for the compound of Example 12. The crude product was subjected to column chromatography (SiO$_2$, 75% ethyl acetate in hexane) to give the title compound as a yellow solid (30 mg) m.p. 133–135°. δH (CDCl$_3$) 7.52 (2H, d, J 8.1 Hz), 7.38 (4H, m), 7.28 (2H, d, J 7.4 Hz), 5.40 (4H, m), 2.40 (3H, s) and 2.23 (3H, s).

EXAMPLE 18
5-Amino-1-(4-methoxyphenyl)-3-(4-tolyl)pyrazole-4-carboxamide

The title compound was prepared from 2-cyano-3-methylthio-3-(4-tolyl)acrylamide (232 mg, 1.0 mmol), 4-methoxyphenylhydrazine hydrochloride (192 mg, 1.1 mmol) and sodium hydroxide (44 mg, 1.1 mmol) following the procedure used for the compound of Example 12. The crude product was purified by chromatography (SiO$_2$, 75% ethyl acetate in hexane) and recrystallisation from ethyl acetate-hexane to give the title compound as white crystals (101 mg) m.p. 174–175°. δH (d$^6$DMSO) 7.49–7.43 (4H, m), 7.28 (2H, d, J 7.8 Hz), 7.07 (2H, d, J 8.9 Hz), 6.32 (2H, br s), 3.81 (3H, s) and 2.29 (3H, s), one set of amino protons not observed. MS (ES$^+$) 323 (MH$^+$, 100%).

EXAMPLE 19
5-Amino-1-(4-nitrophenyl)-3-(4-tolyl)pyrazole-4-carboxamide

The title compound was prepared from 2-cyano-3-methylthio-3-(4-tolyl)acetamide (464 mg, 2.0 mmol) and 4-nitrophenylhydrazine (337 mg, 2.2 mmol) following the procedure used for the compound of Example 12. The crude product was purified by column chromatography (SiO$_2$, 2% acetic acid, 5% methanol in CH$_2$Cl$_2$) to give the title compound as a yellow solid (14 mg) m.p. 299–3000. δH (d$^6$DMSO) 8.42 (2H, d, J 8.6 Hz), 8.21 (2H, d, J 8.7 Hz), 7.80 (2H, d, J 8.0 Hz) and 7.75 (2H, d, J 7.9 Hz).

EXAMPLE 20
5-Amino-1-(3-nitrophenyl)-3-(4-tolyl)pyrazole-4-carboxamide

The title compound was prepared from 2-cyano-3-methylthio-3-(4-tolyl)acrylamide (464 mg, 2.0 mmol), 3-nitrophenylhydrazine hydrochloride (417 mg, 2.2 mmol) and sodium hydroxide (88 mg, 2.2 mmol) following the procedure used for the compound of Example 12. The crude product was purified by column chromatography (SiO$_2$, 50% ethyl acetate in hexane) and recrystallisation from ethyl acetate to give the title compound as white crystals (50 mg) m.p. 237–238°. δH (d$^6$DMSO) 8.42 (1H, s), 8.21 (1H, d, J 7.8 Hz), 8.11 (1H, d, J 7.8 Hz), 7.79 (1H, t, J 8.2 Hz), 7.50 (2H, d, J 8.0 Hz), 7.30 (2H, d, J 8.1 Hz), 6.70 (2H, s), 5.50 (2H, br s) and 2.37 (3H, s).

EXAMPLE 21
5-Amino-1-(3-aminophenyl)-3-(4-tolyl)pyrazole-4-carboxamide

10% Palladium on carbon (100 mg) was added to a de-gassed solution of the compound of Example 20 (120 mg, 0.36 mmol) and ammonium formate (30 mg, 4.8 mmol) in methanol. The reaction was stirred at room temperature and under nitrogen for 18 h. The reaction mixture was filtered through a pad of Celite® and ethanol removed under reduced pressure. The residue was purified by column chromatography (SiO$_2$, ethyl acetate) to give the title compound (13 mg) as yellow crystals after trituration with diethyl ether m.p. 220–222°. δH (CDCl$_3$) 7.45 (2H, d, J 8.0 Hz), 7.30–7.20 (3H, m), 6.90 (1H, d, J 7.9 Hz), 6.81 (1H, s), 6.62 (1H, d, J 8.0 Hz), 5.41 (2H, br s), 2.63 (2H br s) and 2.39 (3H, s). MS (ES$^+$) 308 (MH$^+$, 100%).

EXAMPLE 22
5-Amino-1-(3-hydroxypropyl)-3-(4-tolyl)pyrazole-4-carboxamide

The title compound was prepared from 2-cyano-3-methylthio-3-(4-tolyl)acrylamide (464 mg, 2.0 mmol), sodium carbonate (424 mg, 4.0 mmol) and 1-(3-hydroxypropyl)hydrazinium trifluoroacetate (449 mg, 2.2 mmol) following the procedure used for the compound of Example 12. The crude product was subjected to column chromatography (SiO$_2$, 8% methanol in CH$_2$Cl$_2$) and was recrystallised from ethyl acetate to give the title compound as white crystals (240 mg) m.p. 164–165°. δH (CDCl$_3$) 7.43 (2H, d, J 8.1 Hz), 7.26 (2H, d, J 7.8 Hz), 5.73 (2H, br s), 5.18 (2H, br s), 4.12 (2H, t, J 6.1 Hz), 3.66 (2H, t, J 5.5 Hz), 2.40 (3H, s), 2.04 (2H, quintet, J 6.1 Hz) and 1.59 (1H, br s).

The hydrazine starting material was prepared following the method of A. Collet et al J. Org. Chem. 1993, 58, 4791–4793. A solution of N-(tert-butoxycarbonyl)-3-(4-cyanophenyl)-oxaziridine (1.03 g, 4.2 mmol) in anhydrous diethyl ether (10 ml) was added to a solution of 3-amino-1-propanol (300 mg, 4.0 mmol) in diethyl ether (10 ml) and the mixture stirred at room temperature for 2 h. Solvent was removed under reduced pressure and the residue puified by chromatography (SiO$_2$, 3–5% methanol in CH$_2$Cl$_2$) to give 3-[1-(tert-butoxycarbonyl)hydrazino]-1-propanol as a white solid (400 mg). δH (CDCl$_3$) 6.14 (1H, br s), 3.78 (2H, t, J 5.6 Hz), 3.04 (2H, t, J 6.1 Hz), 1.71 (2H, quintet, J 6.0 Hz) and 1.46 (9H, s). MS (ES$^+$) 191 (MH$^+$, 100%). Treatment of this compound with trifluoroacetic acid gave the required 1-(3-hydroxypropyl)hydrazinium trifluoroacetate which was used without further purification.

EXAMPLE 23
5-Amino-1-[2-(1-hydroxy-2-methyl)propyl]-3-(4-tolyl)pyrazole-4-carboxamide The title compound was prepared from 2-cyano-3-methylthio-3-(4-tolyl)acrylamide (418 mg, 1.8 mmol), sodium carbonate (424 mg, 4.0 mmol) and 1-[2-(1-hydroxy-2-methyl)propyl]hydrazinium trifluoroacetate (412 mg, 2.0 mmol) following the procedure used for the compound of Example 12. The crude product was subjected to column chromatography (SiO$_2$, 4% methanol in CH$_2$Cl$_2$) to give the title compound as a white solid (150 mg) m.p. 219–220°. δH (CDCl$_3$) 7.43 (2H, d, J 7.8 Hz), 7.26 (2H, d, J 7.8 Hz), 5.78 (2H, br s), 5.22 (2H, br s), 4.22 (1H, t, J 7.1 Hz), 3.88 (2H, d, J 6.6 Hz), 2.40 (3H, s), and 1.58 (6H, s). MS (ES$^+$) 289 (MH$^+$, 100%).

The hydrazine starting material used in the above procedure was obtained from 2-amino-2-methyl-1-propanol (383 mg, 4.3 mmol) in a similar manner to the hydrazine prepared in Example 22. This gave 2-[2-(tert-butoxy-carbonyl)hydrazino]-2-methyl-1-propanol as a clear gum (400 mg). δH (CDCl$_3$) 6.39 (1H, br s), 3.19 (2H, s), 1.42 (9H, s) and 0.97 (6H, s).

Treatment of this compound with trifluoracetic acid gave the required 1-[2-(1-hydroxy-2-methyl)propyl]hydrazinium trifluoroacetate which was used without further purification.

EXAMPLE 24
5-Amino-1-(3-carboxyphenyl)-3-(4-tolyl)pyrazole-4-carboxamide

The title compound was prepared from 2-cyano-3-methylthio-3-(4-tolyl)acrylamide (464 mg, 2.0 mmol), 3-carboxyphenylhydrazine (304 mg, 2.0 mmol) and triethylamine (2 ml) following the procedure used for the compound of Example 12. The crude product was subjected to column chromatography (SiO$_2$, 2% acetic acid, 5% methanol in CH$_2$Cl$_2$) to give the title compound as a light yellow solid (340 mg) m.p. 232–235°. δH (d$^6$DMSO) 8.14 (1H, s), 7.93 (1H, d, J 7.9 Hz), 7.86 (1H, d, J 9.0 Hz), 7.64 (1H, t, J 7.8 Hz), 7.47 (2H, d, J 8.1 Hz), 7.30 (2H, d, J 8.1 Hz), 6.55 (1H, br s), 6.53 (1H, br s) and 2.36 (3H, s), carboxyl proton and amino protons not observed. MS (ES, +27V) 337 (MH$^+$, 100%);

EXAMPLE 25
5-Amino-1-(4-carboxyphenyl)-3-(4-tolyl)pyrazole-4-carboxamide

The title compound was prepared from 2-cyano-3-methylthio-3-(4-tolyl)-acrylamide (464 mg, 2.0 mmol) and 4-hydrazinobenzoic acid (334 mg, 2.2 mmol) following the procedure used for the compound of Example 12. The crude product was purified by column chromatography (SiO$_2$, 5–10% methanol +2% acetic acid in CH$_2$Cl$_2$) and by trituration with methanol to give the title compound as a light yellow solid (497 mg) m.p. >310° dec. δH (d$^6$DMSO) 8.06 (2H, d, J 8.7 Hz), 7.75 (2H, d, J 8.6 Hz), 7.48 (2H, d, J 8.1 Hz), 7.29 (2H, d, J 8.0 Hz), 6.63 (2H, br s) and 2.36 (3H, s), carboxyl proton and amino protons not observed.

EXAMPLE 26
5-Amino-1-{3-[N-(N'-tert-butoxycarbonyl)-2-aminoethyl)]benzamido}-3-(4-tolyl)pyrazole-4-carboxamide To a solution of the compound of Example 24 (150 mg, 0.45 mmol), N-hydroxysuccinimide (59 mg, 0.51 mmol), N-methylmorpholine (0.5 ml, 4.50 mmol) and N-(tert-butoxycarbonyl)ethylenediamine (82 mg, 0.51 mmol) in anhydrous DMF (15 ml) was added 1-(3-dimethylaminopropyl)-3-ethylcarbodiimide hydrochloride (96 mg, 0.51 mmol) and the mixture stirred at room temperature for 20 h. The reaction was partitioned between ethyl acetate (50 ml) and water (50 ml). The layers were separated and the aqueous extracted with further portions of ethyl acetate (25 ml x 2). The combined ethyl acetate extracts were washed with brine (50 ml), dried (MgSO$_4$) and concentrated under reduced pressure to give a yellow solid. The crude product was subjected to column chromatography (SiO$_2$, 4–5% methanol in CH$_2$Cl$_2$) to give the title compound as a white solid (100 mg). δH (d$^6$DMSO) 8.57 (1H, t, J 6.9 Hz), 8.03 (1H, s), 7.83 (1H, d, J 7.7 Hz), 7.74 (1H, d, J 8.9 Hz), 7.61 (1H, t, J 7.9 Hz), 7.45 (2H, d, J 8.1 Hz), 7.30 (2H, d, J 8.1 Hz), 6.88 (1H, t, J 6.9 Hz), 6.55 (2H, br s), 3.38 (2H, m), 3.10 (2H, q, J 6.0 Hz), 2.36 (3H, s) and 1.35 (9H, s). MS (ES$^+$) 479 (MH$^+$, 100%).

EXAMPLE 27
5-Amino-1-[3-(N-{2-aminoethyl}benzamido)]-3-(4-tolyl)pyrazole-4-carboxamide trifluoroacetate Trifluoroacetic acid (10 ml) was added to a suspension of the compound of Example 26 (100 mg, 0.21 mmol) in CH$_2$Cl$_2$ (10 ml). After 20 minutes the reaction mixture was concentrated under reduced pressure and the product triturated with diethyl ether to give the title compound as a buff powder (75 mg). δH (d$^6$DMSO) 8.70 (1H, t, J 3.7 Hz), 8.06 (1H, s), 7.87 (1H, d, J 7.3 Hz), 7.78 (3H, m), 7.64 (1H, t, J 7.3 Hz), 7.45 (2H, d, J 8.0 Hz), 7.30 (2H, d, J 8.0 Hz), 6.55 (2H, br s), 3.53 (2H, q, J 7.0 Hz), 3.01 (2H, m) and 2.39 (3H, s). MS (ES$^+$) 379 (MH$^+$, 100%), 362 (MH$^+$ —NH$_3$, 45%).

EXAMPLE 28
5-Amino-1-{3-[N-(N'-(tert-butoxycarbonyl)-3-aminopropyl)]benzamido}-3-(4-tolyl)pyrazole-4-carboxamide The title compound was prepared from the compound of Example 24 (215 mg, 0.64 mmol) and N-(tert-butoxycarbonyl)-1,3-diaminopropane (134 mg, 0.77 mmol) following the procedure used for the compound of Example 26. The crude product was purified by column chromatography (SiO$_2$, 5% methanol in CH$_2$Cl$_2$) to give the title compound as a white solid (80 mg) m.p. 111–113°. δH (d$^6$DMSO) 8.55 (1H, t, J 6.2 Hz), 8.03 (1H, s with fine coupling), 7.83 (1H, d, J 7.9 Hz), 7.75 (1H, d, J 8.9 Hz), 7.61 (1H, t, J 7.9 Hz), 7.46 (2H, d, J 8.1 Hz), 7.30 (2H, d, J 8.1 Hz), 6.78 (1H, t, J 6.2 Hz), 6.55 (2H, br s), 3.25 (2H, q, J 6.6 Hz), 2.96 (2H, q, J 6.3 Hz), 2.36 (3H, s), 1.63 (2H, quintet, J 6.9 Hz), and 1.36 (9H, s).

EXAMPLE 29
5-Amino-1-[3-(N-{3-aminopropyl}benzamido)]-3-(4-tolyl)pyrazole-4-carboxamide trifluoroacetate The title compound was prepared by treating the compound of Example 28 (80 mg, 0.17 mmol) with trifluoroacetic acid following the procedure used for the compound of Example 27. This gave the title compound as a white solid (86 mg). δH (CDCl$_3$) 8.74 (1H, t, J 5.9 Hz), 8.04 (1H, s), 7.85 (1H, d, J 7.8 Hz), 7.79 (3H, m), 7.62 (1H, t, J 7.9 Hz), 7.45 (2H, d, J 8.0 Hz), 7.30 (2H, d, J 7.9 Hz), 6.56 (2H, br s), 3.56 (2H, br s), 3.34 (2H, q, J 5.9 Hz), 2.84 (2H, br s), 2.36 (3H, s) and 1.80 (2H, quintet, J 7.0 Hz). MS (ES$^+$) 393 (MH$^+$, 100%).

EXAMPLE 30
5-Amino-1-{4-[N-(N'-(tert-butoxycarbonyl)-3-aminopropyl)]benzamido}-3-(4-tolyl)pyrazole-4-carboxamide The title compound was prepared from the compound of Example 25 (160 mg, 0.49 mmol) and N-(tert-butoxycarbonyl)-1,3-diaminopropane (101 mg, 0.58 mmol)

following the procedure used for the compound of Example 26. The crude product was purified by column chromatography (SiO$_2$, 5% methanol in CH$_2$Cl$_2$) to give the title compound as an orange solid (135 mg) m.p. 109–110°. δH (d$^6$DMSO) 8.51 (1H, t, J 3.8 Hz), 7.97 (2H, d, J 8.5 Hz), 7.71 (2H, d, J 8.6 Hz), 7.43 (2H, d, J 8.0 Hz), 7.30 (2H, d, J 8.3 Hz), 6.84 (1H, t, J 2.0 Hz), 6.59 (2H, s), 3.28 (2H, m), 2.97 (2H, m), 2.36 (3H, s), 1.65 (1H, m) and 1.36 (9H, s). MS (ES$^+$) 493 (MH$^+$, 100%).

EXAMPLE 31

5-Amino-1-[4-(N-{3-aminopropyl})benzamido]-3-(4-tolyl)pyrazole-4-carboxamide trifluoroacetate The title compound was prepared by treating the compound of Example 30 (110 mg, 0.22 mmol) with trifluoroacetic acid following the procedure used for the compound of Example 27. This gave the title compound as pale pink crystals (30 mg) m.p. 118–120°. δH (d$^6$DMSO) 8.70 (1H, t, J 3.5 Hz), 8.00 (2H, d, J 8.6 Hz), 7.75 (2H, d, J 8.5 Hz), 7.45 (2H, d, J 7.9 Hz), 7.30 (2H, d, J 7.7 Hz), 6.59 (1H, m), 3.35 (2H, m), 2.84 (2H, m), 2.36 (3H, s) and 1.81 (2H, m). MS (ES$^+$) 393 (MH$^+$, 100%).

BIOLOGICAL ACTIVITY

The following assays were used to demonstrate the activity and selectivity of compounds according to the invention. Enzymes for the assays were either obtained commercially or purified from known natural or recombinant sources using conventional methods.

p56$^{lck}$ kinase assay

The tyrosine kinase activity of p56$^{lck}$ was determined using a RR-src peptide (RRLIEDNEYTARG) and [γ-$^{33}$P] ATP as substrates. Quantitation of the $^{33}$P-phosphorylated peptide formed by the action of p56$^{lck}$ was achieved using an adaption of the method of Geissler et al (J. Biol. Chem. (1990) 265, 22255–22261).

All assays were performed in 20 mM HEPES pH 7.5 containing 10 mM MgCl$_2$, 10 mM MnCl$_2$, 0.05% Brij, 1 μM ATP (0.5μCi[γ-$^{33}$P]ATP) and 0.8 mg/ml RR-src. Inhibitors in dimethylsulphoxide (DMSO) were added such that the final concentration of DMSO did not exceed 1%, and enzyme such that the consumption of ATP was less than 10%. After incubation at 30° C. for 15 min, the reaction was terminated by the addition of one-third volume of stop reagent (0.25 mM EDTA and 33 mM ATP in dH$_2$O). A 15 μl aliquot was removed, spotted onto a P-30 filtermat (Wallac, Milton Keynes, UK), and washed sequentially with 1% acetic acid and dH$_2$O to remove ATP. The bound $^{33}$P-RR-src was quantitated by scintillation counting of the filtermat in a Betaplate scintillation counter (Wallac, Milton Keynes, UK) after addition of Meltilex scintillant (Wallac, Milton Keynes, UK).

The dpm obtained, being directly proportional to the amount of $^{33}$P-RR-src produced by p56$^{lck}$, were used to determine the IC$_{50}$ for each compound. The IC$_{50}$ was defined as the concentration of compound required to reduce the production of $^{33}$P-RR-src by 50%.

In this test, compounds according to the invention, such as the compounds of the Examples, have IC$_{50}$ values of around 5 μM and below.

Zap-70 and Csk kinase assays

Inhibitor activity against Zap-70 or Csk kinase was determined using a capture assay based on that employed above for p56$^{lck}$ but with the following modifications. The RR-src peptide was replaced with polyGlu-Tyr (Sigma; Poole, UK) at a final concentration of 17 μg/ml. After addition of the stopped reaction to the filtermat, trichloroacetic acid 10% (w/v) was employed as the wash reagent instead of acetic acid and a final wash in absolute ethanol was also performed before scintillation counting. In these assays, compounds of the invention, such as the compounds of the Examples had little or no measurable activity against either Zap-70 or Csk kinases.

Protein kinase C assay

Inhibitor activity against protein kinase C (PKC) was determined using PKC obtained from Sigma Chemical Company (Poole, UK) and a commercially available assay system (Amersham International plc, Amersham, UK). Briefly, PKC catalyses the transfer of the γ-phosphate ($^{32}$p) of ATP to the threonine group on a peptide specific for PKC. Phosphonylated peptide is bound to phosphocellulose paper and subsequently quantified by scintillation counting. The inhibitor potency is expressed as either (i) the concentration required to inhibitor 50% of the enzyme activity (IC$_{50}$) or (ii) the percentage inhibition achieved by 10 μM inhibitor. In this assay, compounds of the invention, such as the compounds of the Examples had little or no measurable activity at concentrations at which they inhibit the activity of p561$^{lck}$.

We claim:

1. A compound of formula (1):

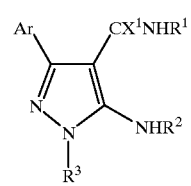

wherein:

Ar is an optionally substituted aromatic or heteroaromatic group;

X$^1$ is an oxygen or sulphur atom;

R$^1$ is a hydrogen atom or a methyl group;

R$^2$ is a hydrogen atom or a group —Alk$^1$ or —X$^2$Alk$^1$, where Alk$^1$ is an optionally substituted aliphatic or heteroaliphatic group and X$^2$ is a —C(O)—, —C(S)—, or —S(O)$_n$— group where n is an integer 1 or 2;

R$^3$ is a hydrogen atom or a group —Alk$^2$, —X$^2$Alk$^2$, —Ar$^1$, —Alk$^2$Ar$^1$ or —X$^2$Alk$^2$Ar$^1$, where Alk$^2$ is an optionally substituted aliphatic or heteroaliphatic group and Ar$^1$ is an optionally substituted aromatic or heteroaromatic group;

and the salts, solvates, hydrates and N-oxides thereof;

with the proviso that when X$^1$ is an oxygen atom, R$^1$ is a hydrogen atom, R$^2$ is a hydrogen atom or a C$_{1-3}$alkyl or —C(O)—Alk$^1$ group, where Alk$^1$ is C$_{1-4}$alkyl, and R$^3$ is a C$_{1-5}$alkyl group which is unsubstituted or substituted with a halogen atom or a hydroxyl group, then Ar is other than a 5-nitro-2-imidazolyl or 5-nitro-2-furyl group.

2. A compound according to claim 1 wherein X$^1$ is an oxygen atom.

3. A compound according to claim 2 wherein R$^1$ and R$^2$ is each a hydrogen atom.

4. A compound according to claim 3 wherein R$^3$ is an —Alk$^2$, —X$^2$Alk$^2$, —Ar$^1$, —Alk$^2$Ar$^1$ or —X$^2$Alk$^2$Ar$^1$ group.

5. A compound according to claim 4 wherein R$^3$ is an —Alk$^2$ or —Ar$^1$ group.

6. A pharmaceutical composition comprising a compound of formula (1):

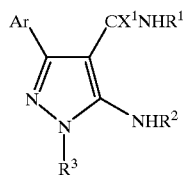

(1)

wherein:
Ar is an optionally substituted aromatic or heteroaromatic group;
$X^1$ is an oxygen or sulphur atom;
$R^1$ is a hydrogen atom or a methyl group;
$R^2$ is a hydrogen atom or a group —$Alk^1$ or —$X^2Alk^1$, where $Alk^1$ is an optionally substituted aliphatic or heteroaliphatic group and $X^2$ is a —C(O)—, —C(S)—, or —$S(O)_n$— group where n is an integer 1 or 2;
$R^3$ is a hydrogen atom or a group —$Alk^2$, —$X^2Alk^2$, —$Ar^1$, —$Alk^2Ar^1$ or —$X^2Alk^2Ar^1$, where $Alk^2$ is an optionally substituted aliphatic or heteroaliphatic group and $Ar^1$ is an optionally substituted aromatic or heteroaromatic group;
and the salts, solvates, hydrates and N-oxides thereof;
with the proviso that when $X^1$ is an oxygen atom, $R^1$ is a hydrogen atom, $R^2$ is a hydrogen atom or a $C_{1-3}$alkyl or —C(O)—$Alk^1$ group, where $Alk^1$ is $C_{1-4}$alkyl, and $R^3$ is a $C_{1-5}$alkyl group which is unsubstituted or substituted with a halogen atom or a hydroxyl group, then Ar is other than a 5-nitro-2-imidazolyl or 5-nitro-2-furyl group; together with one or more pharmaceutically acceptable carriers, excipients or diluents.

7. A method for the prophylaxis or treatment of a disease or disorder in a mammal in which inappropriate protein tyrosine kinase action plays a role, which comprises administering to a mammal suffering from such a disease or disorder a therapeutically effective amount of a compound of formula (1):

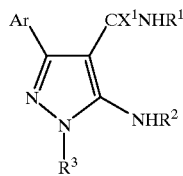

(1)

wherein:
Ar is an optionally substituted aromatic or heteroaromatic group;
$X^1$ is an oxygen or sulphur atom;
$R^1$ is a hydrogen atom or a methyl group;
$R^2$ is a hydrogen atom or a group —$Alk^1$ or —$X^2Alk^1$, where $Alk^1$ is an optionally substituted aliphatic or heteroaliphatic group and $X^2$ is a —C(O)—, —C(S)—, or —$S(O)_n$— group where n is an integer 1 or 2;
$R^3$ is a hydrogen atom or a group —$Alk^2$, —$X^2Alk^2$, —$Ar^1$, —$Alk^2Ar^1$ or —$X^2Alk^2Ar^1$, where $Alk^2$ is an optionally substituted aliphatic or heteroaliphatic group and $Ar^1$ is an optionally substituted aromatic or heteroaromatic group;
and the salts, solvates, hydrates and N-oxides thereof.

8. A compound according to claim 3 wherein Ar is an optionally substituted aromatic group.

9. A compound according to claim 8 wherein Ar is a monocyclic or bicyclic $C_{6-12}$ optionally substituted aromatic group.

10. A compound according to claim 9 wherein Ar is an optionally substituted phenyl, 1- or 2-naphthyl, 1- or 2-tetrahydronaphthyl, indanyl or indenyl group.

11. A compound according to claim 1 which is 5-amino-1-tert-butyl-3-(4'-chlorophenyl)pyrazole-4-carboxamide, and the salts, solvates, hydrates and N-oxides thereof.

12. A compound according to claim 10 wherein Ar is an optionally substituted phenyl group.

13. A compound according to claim 5 wherein $Ar^1$ is a monocyclic or bicyclic $C_{6-12}$ optionally substituted aromatic group or a monocyclic or bicyclic $C_{5-13}$ optionally substituted heteroaromatic group containing 1 to 4 heteroatoms selected from oxygen, sulphur and nitrogen atoms.

14. A compound according to claim 13 wherein $R^3$ is an optionally substituted $C_{1-6}$alkyl, an optionally substituted phenyl or an optionally substituted pyridyl group.

15. A method according to claim 7 wherein said protein tyrosine kinase is $p56^{lck}$.

16. A method according to claim 7 wherein said disease or disorder is selected from the group consisting of autoimmune diseases, transplant rejection, grant versus host disease, hyperproliferative disorders, and diseases in which cells receive pro-inflammatory signals.

* * * * *